(12) United States Patent
Dou et al.

(10) Patent No.: US 10,909,682 B2
(45) Date of Patent: Feb. 2, 2021

(54) METHOD AND DEVICE FOR DETECTING PULMONARY NODULE IN COMPUTED TOMOGRAPHY IMAGE, AND COMPUTER-READABLE STORAGE MEDIUM

(71) Applicant: SHENZHEN IMSIGHT MEDICAL TECHNOLOGY CO. LTD., Guangdong (CN)

(72) Inventors: Qi Dou, Guangdong (CN); Quande Liu, Guangdong (CN); Hao Chen, Guangdong (CN)

(73) Assignee: SHENZHEN IMSIGHT MEDICAL TECHNOLOGY CO. LTD., Shenzhen (CN)

(*) Notice: Subject to any disclaimer, the term of this patent is extended or adjusted under 35 U.S.C. 154(b) by 157 days.

(21) Appl. No.: 16/243,217

(22) Filed: Jan. 9, 2019

(65) Prior Publication Data
US 2020/0005460 A1 Jan. 2, 2020

(30) Foreign Application Priority Data
Jun. 28, 2018 (CN) .......................... 2018 1 0695624

(51) Int. Cl.
*G06T 7/00* (2017.01)
*G06T 7/143* (2017.01)
(Continued)

(52) U.S. Cl.
CPC ............ *G06T 7/0016* (2013.01); *A61B 6/032* (2013.01); *A61B 6/50* (2013.01); *A61B 6/5205* (2013.01);
(Continued)

(58) Field of Classification Search
CPC ......... G06T 7/0016; G06T 7/143; G06T 7/11; G06T 2207/10081; G06T 2207/20076;
(Continued)

(56) References Cited

U.S. PATENT DOCUMENTS

2009/0092299 A1* 4/2009 Jerebko .................. G06K 9/622
382/128
2018/0089840 A1 3/2018 Zhennan et al.
(Continued)

FOREIGN PATENT DOCUMENTS

CN 105976367 A 9/2016
CN 106650830 A 5/2017
(Continued)

OTHER PUBLICATIONS

Jiang et al., S.F., Data-fusion damage detection approach based on probabilistic neural network classifier, Chinese Journal of Computational Mechanics, vol. 25, No. 5, Oct. 2008, pp. 700-705.
(Continued)

Primary Examiner — Michael R Neff
(74) Attorney, Agent, or Firm — Hauptman Ham, LLP (57) ABSTRACT

Disclosed are a method and a device for detecting pulmonary nodule in Computed Tomography (CT) image, as well as a computer-readable storage medium. The method for detecting pulmonary nodule in CT image includes: obtaining a CT image to be detected, performing a pixel segmentation processing on the CT image through a pre-stored three-dimensional convolutional neural pixel segmentation network, to obtain a probability graph corresponding to the CT image, and obtaining a candidate nodule region by marking a connected domain on the probability graph; and predicting the candidate nodule region by various pre-stored prediction models corresponding to different three-dimensional convolutional neural network classifiers, to obtain various prob-
(Continued)

ability prediction values of the candidate nodule region, and comprehensively processing the various probability prediction values to obtain a classification result of the candidate nodule region.

18 Claims, 2 Drawing Sheets

(51) Int. Cl.
*G06T 7/11* (2017.01)
*A61B 6/03* (2006.01)
*A61B 6/00* (2006.01)
*G06K 9/62* (2006.01)

(52) U.S. Cl.
CPC ......... *G06K 9/6262* (2013.01); *G06K 9/6277* (2013.01); *G06T 7/11* (2017.01); *G06T 7/143* (2017.01); *G06T 2207/10081* (2013.01); *G06T 2207/20076* (2013.01); *G06T 2207/20081* (2013.01); *G06T 2207/20084* (2013.01); *G06T 2207/30064* (2013.01)

(58) Field of Classification Search
CPC . G06T 2207/20081; G06T 2207/20084; G06T 2207/30064; A61B 6/032; A61B 6/50; A61B 6/5205; G06K 9/6262; G06K 9/6277
USPC .......................................................... 382/131
See application file for complete search history.

(56) References Cited

U.S. PATENT DOCUMENTS

2018/0365829 A1* 12/2018 Madabhushi ........... G06T 7/174
2019/0050982 A1*  2/2019 Song ......................... G06T 7/70

FOREIGN PATENT DOCUMENTS

| CN | 106780460 A | 5/2017 |
|----|-------------|--------|
| CN | 106940816 A | 7/2017 |
| CN | 107480677 A | 12/2017 |
| CN | 107590797 A | 1/2018 |
| CN | 108010021 A | 5/2018 |
| CN | 108257128 A | 7/2018 |

OTHER PUBLICATIONS

Da Zhong, Ke Ji., No. 9, Sep. 2011, (Cumulatively No. 145), pp. 30-32.
Journal of Henan University of Science and Technology (Natural Science), vol. 38, No. 3, Jun. 2017, pp. 41-46.
Xu et al., F., "High Resolution Remote Sensing Image Classification Combining with Mean—Shift Segmentation and Fully Convolution Neural Network," Laser & Optoelectronics Progress, 55, 022802 (2018), pp. 022802-1 to 022802-9.
Chinese Office Action issued in corresponding Chinese Application No. 201810695624.8 dated Mar. 2, 2020.
International Search Report issued in International Application No. PCT/CN2018/104189 dated Mar. 29, 2019.
Second Chinese Office Action issued in corresponding Chinese Application No. 201810695624.8, dated Jul. 10, 2020, pp. 1-9, State Intellectual Property Office of People's Republic of China, Beijing, China.

* cited by examiner

METHOD AND DEVICE FOR DETECTING PULMONARY NODULE IN COMPUTED TOMOGRAPHY IMAGE, AND COMPUTER-READABLE STORAGE MEDIUM

TECHNICAL FIELD

The present disclosure relates to the field of image processing technology, and more particularly relates to a method and a device for detecting pulmonary nodule in computed tomography (CT) image, as well as a computer-readable storage medium.

BACKGROUND

Pulmonary nodule is one of the most important early signs of lung cancer. The pathological changes of lung lesions can be inferred according to the lesion characteristics of the pulmonary nodule. Due to the uncertainty of the features, such as size, shape, and density of nodules, the methods of detecting pulmonary nodule in the prior art can hardly satisfy the market demand for pulmonary nodule detection accuracy.

SUMMARY

It is therefore one main object of the present disclosure to provide a method and a device for detecting pulmonary nodule in CT image as well as a computer-readable storage medium, aiming to solve the technical problem in the prior art that the accuracy of automatically detecting pulmonary nodules in CT image is poor.

To achieve the above object, this disclosure provides a method for detecting pulmonary nodule in CT image, the method includes the following operations: obtaining a Computed Tomography image to be detected, performing a pixel segmentation processing on the CT image through a pre-stored three-dimensional convolutional neural pixel segmentation network, obtaining a probability graph corresponding to the CT image, and obtaining a candidate nodule region by marking a connected domain on the probability graph; and predicting the candidate nodule region by various pre-stored prediction models corresponding to different three-dimensional convolutional neural network classifiers, to obtain various probability prediction values of the candidate nodule region, and performing fusion processing on the various probability prediction values to obtain a classification result of the candidate nodule region.

In some embodiments, the operation of performing a pixel segmentation processing on the CT image through a pre-stored three-dimensional convolutional neural pixel segmentation network, obtaining a probability graph corresponding to the CT image, and obtaining a candidate nodule region by marking a connected domain on the probability graph includes the following operations: region dividing the computed tomography image in a preset size to obtain sub-regions of the computed tomography image, respectively down-sampling the sub-regions for preset number of times by the pre-stored three-dimensional pixel segmentation network, and up-sampling the sub-regions for the same preset number of times after the sub-regions being down-sampled; performing feature-bridging and amalgamation processing on the sub-regions obtained respectively after the down-sampling process and the up-sampling process, forming sub probability-graphs that having the same size as the sub-regions; splicing each sub-probability graph for restoration to obtain the probability map corresponding to the computed tomography image; and marking a connected domain on the probability map corresponding to the computed tomography image, to obtain the candidate nodule region.

In some embodiments, the down-sampling process includes convolution, activation, batch standardizing, and pooling processing on the sub-regions, and the up-sampling process includes deconvolution, activation, batch standardizing, and pooling processing on the sub-regions.

In some embodiments, the operation of performing fusion processing on the various probability prediction values to obtain a classification result of the candidate nodule region includes the following operations: averaging the various probability prediction values and obtaining a target probability prediction value of the candidate nodule region; and comparing the target probability prediction value with a pre-stored threshold value, obtaining a comparison result, and obtaining the classification result of the candidate nodule region based on the comparison result. The pre-stored threshold value is determined according to a receiver operating characteristic curve corresponding to the three-dimensional convolutional neural network.

In some embodiments, the operation of predicting the candidate nodule region by various pre-stored prediction models corresponding to different three-dimensional convolutional neural network classifiers, to obtain various probability prediction values of the candidate nodule region includes the following operations: down-sampling and full-connecting the candidate nodule region by various pre-stored prediction models corresponding to the different three-dimensional convolutional neural network classifiers, to obtain various probability prediction values of the candidate nodule region; and down-sampling the candidate nodule region includes convoluting, activating, batch standardizing, and pooling processing the candidate nodule region.

In some embodiments, the method further includes the operation of outputting the target probability prediction value and generating a target prompt message subsequent to the operation of obtaining a target probability prediction value of the candidate nodule region.

In some embodiments, the method further includes the operation of collecting computed tomography image sample data online through multiple processes, taking the collected computed tomography image sample data as a first sample data, and using the first sample data as input data to perform a training on the three-dimensional convolutional neural pixel segmentation network and the three-dimensional convolutional neural network classifier, to obtain hard negative sample data. The hard negative sample data is the unsuccessfully predicted sample data in the first sample data; performing multiple translation and horizontal flip operations on the hard negative sample data to increase the proportion of the hard negative sample data in the first sample data, and taking the sample data that increase the proportion of the hard negative sample data as a second sample data; using the second sample data as input data to train the three-dimensional convolutional neural pixel segmentation network and the three-dimensional convolutional neural network classifier multiple times; and when the predicted accuracy of the trained three-dimensional convolutional neural pixel segmentation network and the trained three-dimensional convolutional neural network classifier reaches a first target accuracy rate and a second target accuracy rate respectively, executing the operation of obtaining the computed tomography image to be detected, prior to the operation of obtaining a computed tomography image to be detected, performing a pixel segmentation processing on the computed tomography image through a pre-stored three-dimensional convolutional neural pixel segmentation network.

This disclosure further provides an equipment for detecting pulmonary nodule in CT image, the equipment includes the following parts: an obtaining module, being configured to obtain a CT image to be detected, performing a pixel segmentation processing on the CT image through a pre-stored three-dimensional convolutional neural pixel segmentation network, obtaining a probability graph corresponding to the CT image, and obtaining a candidate nodule region by marking a connected domain on the probability graph; and a model amalgamating module, being configured to predict the candidate nodule region by various pre-stored prediction models corresponding to different three-dimensional convolutional neural network classifiers, to obtain various probability prediction values of the candidate nodule region, and further configured to perform fusion processing on the various probability prediction values to obtain a classification result of the candidate nodule region.

In some embodiments, the obtaining module includes the following parts: a sub probability-graphs obtaining unit, being configured to perform a region division processing by a preset size on the CT image to obtain sub-regions of the CT image, down-sampling the sub-regions by the pre-stored three-dimensional pixel segmentation network for preset number of times, and performing up-sampling on the sub-regions for the same preset number of times after the down-sampling process; and a feature amalgamating unit, being configured to perform feature-bridging and amalgamation processing on the sub-regions obtained after the down-sampling process and the up-sampling process respectively, forming sub probability-graphs that having the same size as the sub-regions; and a splicing unit, being configured to splice each sub-probability graph for restoration to obtain the probability map corresponding to the CT image; and a connected domain processing unit, being configured to mark a connected domain on the probability map corresponding to the CT image to obtain a candidate nodule region.

In some embodiments, the sub probability-graphs obtaining unit is configured to convolution, activation, batch standardizing, and pooling processing on the sub-regions, and further configured to deconvolution, activation, batch standardizing, and pooling processing on the sub-regions after the down-sampling process.

In some embodiments, the model amalgamating module includes the following parts: an averaging unit, being configured to average the various probability prediction values and obtaining a target probability prediction value of the candidate nodule region; and a comparing unit, being configured to compare the target probability prediction value with a pre-stored threshold value, obtaining a comparison result, and obtaining the classification result of the candidate nodule region based on the comparison result. The pre-stored threshold value is determined according to a ROC curve corresponding to the three-dimensional convolutional neural network.

In some embodiments, the model amalgamating module further includes the model amalgamating unit, being configured to perform down-sampling processing and full-connection processing on the candidate nodule region by various pre-stored prediction models corresponding to different three-dimensional convolutional neural network classifiers, to obtain various probability prediction values of the candidate nodule region. And the model amalgamating unit is further configured to perform convolution, activation, batch standardizing, and pooling processing on the candidate nodule region.

In some embodiments, the equipment further includes an outputting module, being configured to output the target probability prediction value and generating a target prompt message.

In some embodiments, the equipment further includes the following parts: a filtering module, being configured to filter CT image sample data online through multiple processes, taking the collected CT image sample data as the first sample data, and using the first sample data as input data to perform a training on the three-dimensional convolutional neural pixel segmentation network and the three-dimensional convolutional neural network classifier, obtaining hard negative samples. The hard negative sample is the unsuccessfully predicted sample in the first sample data; a hard negative sample data enhancing module, being configured to perform multiple translation and horizontal flip operations on the hard negative sample data to increase the proportion of the hard negative sample data in the first sample data, and taking the sample data that increase the proportion of the hard negative sample data as the second sample data; a training module, being configured to use the second sample data as input data for training the three-dimensional convolutional neural pixel segmentation network and the three-dimensional convolutional neural network classifier multiple times; an executing module, being configured to execute the block of obtaining the CT image to be detected the acquired, when the predicted accuracy of the three-dimensional convolutional neural pixel segmentation network and the three-dimensional convolutional neural network classifier after training reaches the first target accuracy rate and the second target accuracy rate respectively.

In addition, in order to achieve the above object, the present disclosure further provides a device for detecting pulmonary nodule in CT image, the device includes a memory, a processor, a communication bus, and a pulmonary nodule in CT image detecting program stored in the memory. The communication bus is configured to facilitate a communication connection between the processor and the memory. The processor is configured to execute the pulmonary nodule in CT image detecting program to perform the following operations: obtaining a Computed Tomography image to be detected, performing a pixel segmentation processing on the CT image through a pre-stored three-dimensional convolutional neural pixel segmentation network, obtaining a probability graph corresponding to the CT image, and obtaining a candidate nodule region by marking a connected domain on the probability graph; and predicting the candidate nodule region by various pre-stored prediction models corresponding to different three-dimensional convolutional neural network classifiers, to obtain various probability prediction values of the candidate nodule region, and performing fusion processing on the various probability prediction values to obtain a classification result of the candidate nodule region.

In some embodiments, the operation of performing a pixel segmentation processing on the CT image through a pre-stored three-dimensional convolutional neural pixel segmentation network, obtaining a probability graph corresponding to the CT image, and obtaining a candidate nodule region by marking a connected domain on the probability graph includes the following operations: region dividing the computed tomography image in a preset size to obtain sub-regions of the computed tomography image, respectively down-sampling the sub-regions for preset number of times by the pre-stored three-dimensional pixel segmentation network, and up-sampling the sub-regions for the same preset number of times after the sub-regions being down-sampled; performing feature-bridging and amalgamation processing on the sub-regions obtained respectively after the down-sampling process and the up-sampling process, forming sub probability-graphs that having the same size as the sub-regions; splicing each sub-probability graph for restoration to obtain the probability map corresponding to the computed tomography image; and marking a connected domain on the probability map corresponding to the computed tomography image, to obtain the candidate nodule region.

In some embodiments, the down-sampling process includes convolution, activation, batch standardizing, and pooling processing on the sub-regions, and the up-sampling process includes deconvolution, activation, batch standardizing, and pooling processing on the sub-regions.

In some embodiments, the operation of performing fusion processing on the various probability prediction values to obtain a classification result of the candidate nodule region includes the following operations: averaging the various probability prediction values and obtaining a target probability prediction value of the candidate nodule region; and comparing the target probability prediction value with a pre-stored threshold value, obtaining a comparison result, and obtaining the classification result of the candidate nodule region based on the comparison result. The pre-stored threshold value is determined according to a receiver operating characteristic curve corresponding to the three-dimensional convolutional neural network.

In some embodiments, the operation of predicting the candidate nodule region by various pre-stored prediction models corresponding to different three-dimensional convolutional neural network classifiers, to obtain various probability prediction values of the candidate nodule region includes the following operations: down-sampling and full-connecting the candidate nodule region by various pre-stored prediction models corresponding to the different three-dimensional convolutional neural network classifiers, to obtain various probability prediction values of the candidate nodule region; and down-sampling the candidate nodule region includes convoluting, activating, batch standardizing, and pooling processing the candidate nodule region.

In some embodiments, the device further includes the operation of outputting the target probability prediction value and generating a target prompt message subsequent to the operation of obtaining a target probability prediction value of the candidate nodule region.

In some embodiments, the device further includes the operation of collecting computed tomography image sample data online through multiple processes, taking the collected computed tomography image sample data as a first sample data, and using the first sample data as input data to perform a training on the three-dimensional convolutional neural pixel segmentation network and the three-dimensional convolutional neural network classifier, to obtain hard negative sample data. The hard negative sample data is the unsuccessfully predicted sample data in the first sample data; performing multiple translation and horizontal flip operations on the hard negative sample data to increase the proportion of the hard negative sample data in the first sample data, and taking the sample data that increase the proportion of the hard negative sample data as a second sample data; using the second sample data as input data to train the three-dimensional convolutional neural pixel segmentation network and the three-dimensional convolutional neural network classifier multiple times; and when the predicted accuracy of the trained three-dimensional convolutional neural pixel segmentation network and the trained three-dimensional convolutional neural network classifier reaches a first target accuracy rate and a second target accuracy rate respectively, executing the operation of obtaining the computed tomography image to be detected, prior to the operation of obtaining a computed tomography image to be detected, performing a pixel segmentation processing on the computed tomography image through a pre-stored three-dimensional convolutional neural pixel segmentation network.

Further, in order to achieve the foregoing object, the present disclosure further provides a computer-readable storage medium that stores one or more programs, which can be executed by one or more processors to perform the following operations: obtaining a Computed Tomography image to be detected, performing a pixel segmentation processing on the CT image through a pre-stored three-dimensional convolutional neural pixel segmentation network, obtaining a probability graph corresponding to the CT image, and obtaining a candidate nodule region by marking a connected domain on the probability graph; and predicting the candidate nodule region by various pre-stored prediction models corresponding to different three-dimensional convolutional neural network classifiers, to obtain various probability prediction values of the candidate nodule region, and comprehensively processing the various probability prediction values to obtain a classification result of the candidate nodule region.

According to this embodiment of pulmonary nodule in computed tomography image detecting method, device and computer readable storage medium, when a Computed Tomography (CT) image to be detected is obtained, performing a pixel segmentation processing on the CT image through a pre-stored three-dimensional convolutional neural pixel segmentation network, obtaining a probability graph corresponding to the CT image, and obtaining a candidate nodule region by marking a connected domain on the probability graph. And the candidate nodule region is predicted by various pre-stored prediction models corresponding to different three-dimensional convolutional neural network classifiers, to obtain various probability prediction values of the candidate nodule region, and comprehensively processing the various probability prediction values to obtain a classification result of the candidate nodule region. This disclosure solves the technical problem in the prior art that the accuracy of automatically detecting pulmonary nodules in CT image is poor.

Various implementations, functional features, and advantages of this disclosure will now be described in further detail in connection with some illustrative embodiments and the accompanying drawings.

DETAILED DESCRIPTION OF ILLUSTRATIVE EMBODIMENTS

It will be appreciated that the specific embodiments described herein are merely illustrative of the disclosure and are not intended to limit the disclosure.

Figure 1:
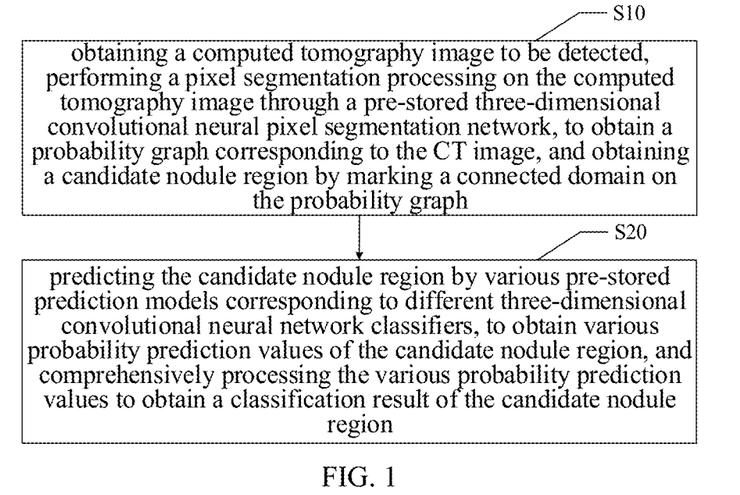
FIG. 1 is an illustrative flowchart of a first embodiment of a method for detecting pulmonary nodule in CT image in accordance with this disclosure.

This disclosure provides a method for detecting pulmonary nodule in CT image. As illustrated in FIG. 1, in a first embodiment of the method for detecting pulmonary nodule in CT image in accordance with the present disclosure, the method includes the following options: obtaining a CT image to be detected, performing a pixel segmentation processing on the CT image through a pre-stored three-dimensional convolutional neural pixel segmentation network, obtaining a probability graph corresponding to the CT image, and obtaining a candidate nodule region by marking a connected domain on the probability graph; and predicting the candidate nodule region by various pre-stored prediction models corresponding to different three-dimensional convolutional neural network classifiers, to obtain various probability prediction values of the candidate nodule region, and performing fusion processing on the various probability prediction values to obtain a classification result of the candidate nodule region.

The followings are specific blocks.

In S10, obtaining a computed tomography image to be detected, performing a pixel segmentation processing on the computed tomography image through a pre-stored three-dimensional convolutional neural pixel segmentation network, to obtain a probability graph corresponding to the computed tomography image, and obtaining a candidate nodule region by marking a connected domain on the probability graph.

Figure 4:
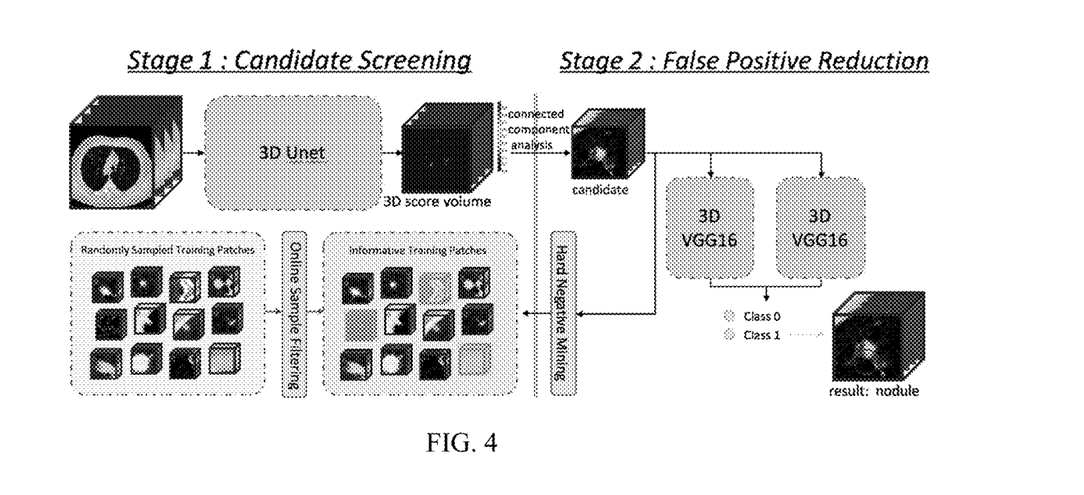
FIG. 4 is a schematic scene diagram of a method for detecting pulmonary nodule in CT image in accordance with this disclosure.

Before performing the detection, firstly acquiring or receiving a computed tomography image to be detected, that is, the CT image. And the CT image is obtained from hospitals by collecting pulmonary nodule from CT images, and the CT image may include the nodule marker region, that is lung nodule region marked the doctor. In this embodiment, after obtaining the CT image, firstly predicting the CT nodule image by using a pre-stored three-dimensional convolutional neural pixel segmentation network to obtain a probability graph corresponding to the CT image, and obtaining a candidate nodule region by analyzing or marking a connected domain on the probability graph. As shown in FIG. 4, 3D-Unet is a three-dimensional convolutional neural pixel segmentation network. Candidate nodule region is obtained through state 1, that is, candidate screening. It should be noted that the three-dimensional convolutional neural pixel segmentation network has been trained already. The last convolutional layer of neural network model is activated by the sigmoid function. The dice and the focal loss function are used in training the pixel segmentation network, in order to alleviate the imbalance of the positive and negative samples.

Figure 2:
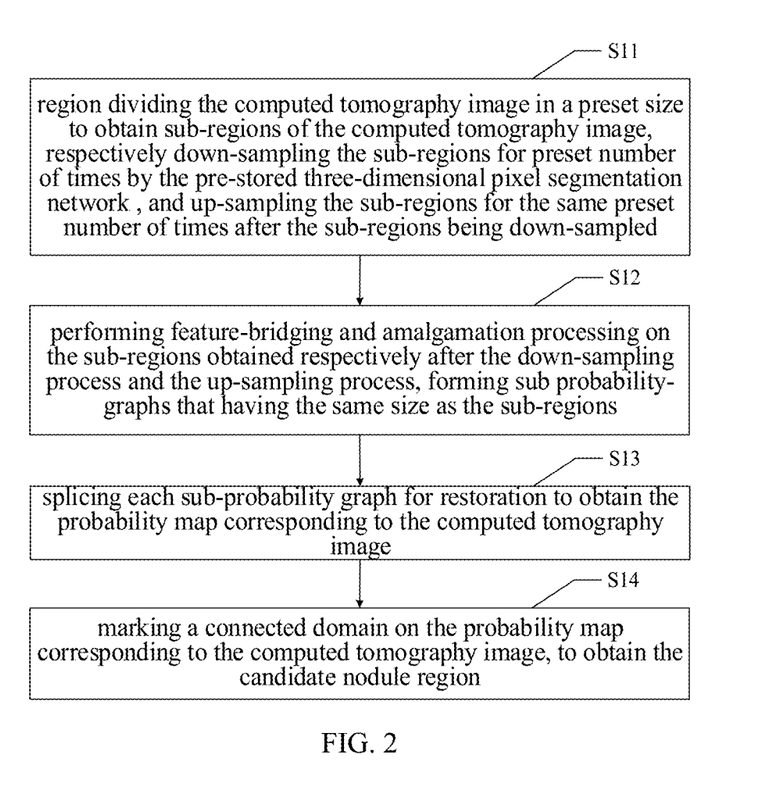
FIG. 2 is an illustrative flowchart of a second embodiment of a method for detecting pulmonary nodule in CT image in accordance with this disclosure.

Specifically, as illustrated in FIG. 2, the block S10 includes the following block S11 to S14.

In S11, region dividing the computed tomography image in a preset size to obtain sub-regions of the computed tomography image, respectively down-sampling the sub-regions for preset number of times by the pre-stored three-dimensional pixel segmentation network, and up-sampling the sub-regions for the same preset number of times after the sub-regions being down-sampled.

In S12, performing feature-bridging and amalgamation processing on the sub-regions obtained respectively after the down-sampling process and the up-sampling process, forming sub probability-graphs that having the same size as the sub-regions.

In S13, splicing each sub-probability graph for restoration to obtain the probability map corresponding to the computed tomography image.

In S14, marking a connected domain on the probability map corresponding to the computed tomography image, to obtain the candidate nodule region.

It should be noted that the storage space of the graphics processor (GPU) is generally difficult to satisfy the simultaneous calculation of the entire CT image, and thus the CT image is subjected to a predetermined size region segmentation process to satisfy the computing power of the GPU, and using the image obtained after the segmentation process as the sub-region of the CT image. For example, during the detection process, the CT image is divided into small regions of 128*128*128, and the small region of 128*128*128 is a sub-region of the CT image.

After obtaining the sub-region of the CT image, the sub-regions of the CT image are separately predicted by the three-dimensional convolutional neural pixel segmentation network to obtain each sub-probability graph. Specifically, down-sampling the sub-regions by the pre-stored three-dimensional pixel segmentation network for preset number of times. And performing up-sampling on the sub-regions for the same preset number of times after the down-sampling process. And performing feature-bridging and amalgamation processing on the sub-regions obtained after the down-sampling process and the up-sampling process respectively, forming sub probability-graphs that having the same size as the sub-regions, to compensate for loss of information in the sub-region caused by the down-sampling process. Since the same number of down-sampling processes and up-sampling processes are performed, sub probability graphs that having the same shape as the sub region of the original CT image can be obtained. The feature-bridging and amalgamation process refers to adding a bridge structure between the same size sub-regions after down-sampling process and up-sampling process during the up-sampling and down-sampling stages, to amalgamate image features of sub-regions, avoiding the loss of possible sub-region information.

Further, performing splicing and restoration on each of the sub-probability graphs can obtain the probability map corresponding to the CT image. By accurately obtaining the probability map, it is possible to lay the foundation for finding candidate nodule regions.

The down-sampling process includes convolution, activation, batch standardizing, and pooling processing on the sub-regions, and the up-sampling process includes deconvolution, activation, batch standardizing, and pooling processing on the sub-regions.

Extracting features of the CT image sub-region. The feature includes image texture features, symmetric features, etc., before the sub probability graphs is obtained, the sub-region needs to be convolved, activated, batch normalized, and pooled by a preset number of times. Among them, the convolution process can be understood as: the statistical characteristics of a part of the image are the same as other parts, that is, the features learned in this part can also be used in other parts, so the learned features are used as detectors, to applicate to anywhere in this image. That is, the feature learned by the small-scale image is convolved with the original large-size image, to achieve obtaining an activation value of a different feature for any pixel position on the image. After the activation value is obtained, the batch standardization process, or correction processing, is performed. The corresponding correction parameter is pre-stored. And after the batch standardization process, the pooling process is performed. In this embodiment, the maximum pooling process may be performed to obtain the maximum activation value, and to extract the local feature. The sub-region after the down-sampling process can be obtained by combining a plurality of local features.

Performing deconvolution, activation, batch standardizing, and pooling processing on the sub-region for the same preset number of times after the down-sampling process to obtain a sub probability graph that having the same size as the sub-region.

The deconvolution process is the reverse process of the convolution process, and will not be specifically described here.

After obtaining the sub probability graphs, splicing and restoring the respective sub probability graphs to obtain a probability graph corresponding to the CT image. The sub probability graph corresponding to the CT image is spliced according to a preset sequence to obtain the probability graph corresponding to the CT image. The preset sequence is associated with a segment order of each sub-region in the pixel segmentation processing on the CT image.

In S20, predicting the candidate nodule region by various pre-stored prediction models corresponding to different three-dimensional convolutional neural network classifiers, to obtain various probability prediction values of the candidate nodule region, and performing fusion processing on the various probability prediction values to obtain a classification result of the candidate nodule region.

It should be noted that, in this embodiment, a plurality of three-dimensional convolutional neural network classifiers are trained, and the prediction models in the different three-dimensional convolutional neural network classifiers are different. Specifically, probability prediction values of the candidate nodule region may be obtained through two prediction models corresponding to the two three-dimensional convolutional nerves network classifier, which is, using two prediction models to predict candidate nodule region, obtaining probability prediction values, and performing fusion processing on the various probability prediction values. As shown in FIG. 4, stage 2. By adopting multiple predictive models, it is possible to eliminate the contingency of the model and improve detection accuracy. After obtaining the various probability prediction values, the classification result of the candidate nodule region can be obtained through the various probability prediction values.

Specifically, the block of predicting the candidate nodule region by various pre-stored prediction models corresponding to different three-dimensional convolutional neural network classifiers, to obtain various probability prediction values of the candidate nodule region includes the following block S21 to S22.

In S21, down-sampling and full-connecting the candidate nodule region by various pre-stored prediction models corresponding to the different three-dimensional convolutional neural network classifiers, to obtain various probability prediction values of the candidate nodule region.

In S22, wherein down-sampling the candidate nodule region includes convoluting, activating, batch standardizing, and pooling processing the candidate nodule region.

It should be noted that different three-dimensional convolutional neural network classifiers respectively predict all candidate nodule regions, and the three-dimensional convolutional neural network classifier includes multiple down-sampling layers and a final fully connected layer to implement down-sampling processing and full-connection processing on each candidate nodule region. The down-sampling process for each candidate nodule region includes convolution, activation, batch standardizing, and pooling processing. And the full connection process is to connect the respective nodes obtained in down-sampling process and perform fusion processing on the image features corresponding to the respective nodes to obtain the probability prediction values of the candidate nodule regions finally. Since the plurality of three-dimensional convolutional neural network classifiers respectively predict each candidate nodule region, and each candidate nodule region gets a probability prediction from each 3D convolutional neural network classifier, so that each candidate nodule region is corresponding to several probability prediction values.

Specifically, the block of comprehensively processing performing fusion processing on the various probability prediction values to obtain a classification result of the candidate nodule region includes the following blocks S23 to S24.

In S23, averaging the various probability prediction values and obtaining a target probability prediction value of the candidate nodule region.

In S24, comparing the target probability prediction value with a pre-stored threshold value, obtaining a comparison result, and obtaining the classification result of the candidate nodule region based on the comparison result. The pre-stored threshold value is determined according to a receiver operating characteristic curve corresponding to the three-dimensional convolutional neural network.

In this embodiment, after obtaining the various probability prediction values corresponding to each candidate nodule region, averaging the various probability prediction values, and using the averaged probability prediction value as a target probability prediction value of the candidate nodule region. After obtaining the target probability prediction value, obtaining a pre-stored threshold value, and comparing the target probability prediction value with the pre-stored threshold to obtain a comparison result. It should be noted that the pre-stored threshold value can be adjusted, specifically, the pre-stored threshold value is determined according to a Receiver Operating Characteristic (ROC) curve corresponding to the three-dimensional convolutional neural network. After obtaining the comparison result, the classification result of the candidate nodule region can be obtained based on the comparison result, and the classification result includes a nodule region and a non-nodular region.

It should be noted that, obtaining a target probability prediction value of the candidate nodule region, outputting the target probability prediction value and generating a target prompt message.

This disclosure obtains a CT image to be detected, performing a pixel segmentation processing on the CT image through a pre-stored three-dimensional convolutional neural pixel segmentation network, obtaining a probability graph corresponding to the CT image, and obtaining a candidate nodule region by marking a connected domain on the probability graph; and predicting the candidate nodule region by various pre-stored prediction models corresponding to different three-dimensional convolutional neural network classifiers, to obtain various probability prediction values of the candidate nodule region, and performing fusion processing on the various probability prediction values to obtain a classification result of the candidate nodule region. In this disclosure, the three-dimensional convolutional neural pixel segmentation network and the three-dimensional convolutional neural network classifier are trained already, they have a certain degree of accuracy. In stage 1, candidate nodule regions are obtained through three-dimensional convolutional neural network. In stage 2, the contingency of different models is compensated through multi-model fusion, and the target probability prediction value of the candidate nodule region is obtained. Therefore, the phenomenon that the detection accuracy of the lung nodules is low due to the uncertainty of the size, shape and density of the pulmonary nodules is avoided, and the technology problem that the existing detection methods are difficult to meet the market demand for the accuracy of the pulmonary nodule detection is solved.

Further, this disclosure provides another embodiment of a method for detecting pulmonary nodule in CT image. In this embodiment, the method further includes the following blocks S01 to S04 prior to the block of obtaining a CT image to be detected, performing a pixel segmentation processing on the CT image through a pre-stored three-dimensional convolutional neural pixel segmentation network.

In S01, collecting computed tomography image sample data online through multiple processes, taking the collected computed tomography image sample data as a first sample data, and using the first sample data as input data to perform a training on the three-dimensional convolutional neural pixel segmentation network and the three-dimensional convolutional neural network classifier, to obtain hard negative sample data, wherein the hard negative sample data is the unsuccessfully predicted sample data in the first sample data.

In S02, performing multiple translation and horizontal flip operations on the hard negative sample data to increase the proportion of the hard negative sample data in the first sample data, and taking the sample data that increase the proportion of the hard negative sample data as the second sample data.

In S03, performing multiple translation and horizontal flip operations on the hard negative sample data to increase the proportion of the hard negative sample data in the first sample data, and taking the sample data that increase the proportion of the hard negative sample data as a second sample data.

In S04, when the predicted accuracy of the trained three-dimensional convolutional neural pixel segmentation network and the trained three-dimensional convolutional neural network classifier reaches a first target accuracy rate and a second target accuracy rate respectively, executing the operation of obtaining the computed tomography image to be detected.

In this embodiment, during the process of training the three-dimensional convolutional neural pixel segmentation network and the three-dimensional convolutional neural network classifier, continuously filtering CT image sample data or the first sample data, online through multiple processes. As shown in FIG. 4, after using the first sample data as input data to perform a training on the three-dimensional convolutional neural pixel segmentation network and the three-dimensional convolutional neural network classifier, enhancing the hard negative sample data by performing multiple translation and horizontal flip operations, to increase the proportion of the hard negative sample data in the second sample data. Therefore, the sensitivity of the convolutional neural network model can be improved during the process of training the three-dimensional convolutional neural network model with the second sample data as input data.

Figure 3:
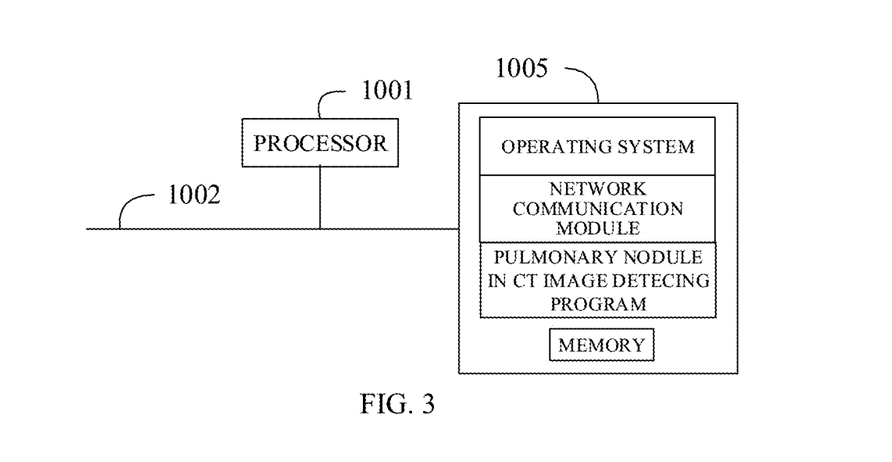
FIG. 3 is a schematic diagram of a device structure in terms of hard operating environment involved in the method embodiments in accordance with this disclosure.

FIG. 3 is a schematic diagram of a device in terms of hard operating environment involved in the method embodiments in accordance with this disclosure.

The device for detecting pulmonary nodule in CT image according to this embodiment of the present disclosure may be a personal computer (PC), laptop, or a terminal device such as a mobile terminal.

As illustrated in FIG. 3, the device for detecting pulmonary nodule in CT image may include a processor 1001 such as a CPU, a memory 1005, and a communication bus 1002. The communication bus 1002 is configured to facilitate connection and communication between the processor 1001 and the memory 1005. The memory 1005 may be a high-speed RAM memory, or a non-volatile memory such as a disk memory. The memory 1005 optionally may also be a storage device that is separate from the processor 1001 described above.

Optionally, the device for detecting pulmonary nodule in CT image may further include a user interface, a network interface, a camera, an RF (Radio Frequency) circuitry, a sensor, an audio circuitry, a Wi-Fi module, and the like. The user interface may include a display, an input unit such as a keyboard, and an optional user interface may also include a standard wired interface and wireless interface. The network interface may optionally include a standard wired interface, and a wireless interface (such as a Wi-Fi interface).

Those skilled in the art can understand that the structure of the device of detecting pulmonary nodule in CT image illustrated in FIG. 3 does not constitute a limitation on the pulmonary nodule in CT image detecting device. Thus, the pulmonary nodule in CT image detecting device may include more or less components than those illustrated, or some components may be combined, or different arrangements of components may be employed.

As illustrated in FIG. 3, the memory 1005 as a computer storage medium may include an operating system, a network communication module, and a pulmonary nodule in CT image detecting program. The operating system is a program that manages and controls the hardware and software resources of the pulmonary nodule in CT image detecting device, and supports the operation of the pulmonary nodule in CT image detecting program and other software and/or programs. The network communication module is configured to facilitate the communication between various components within the memory 1005, and with other hardware and software in the device for detecting pulmonary nodule in CT image.

In the device for detecting pulmonary nodule in CT image as illustrated in FIG. 3, the processor 1001 is configured to execute the pulmonary nodule in CT image detecting program stored in the memory 1005 to perform the blocks in above embodiments of the pulmonary nodule in CT image detecting method.

The specific embodiment of the pulmonary nodule in CT image detecting device of this disclosure is basically the same as the above embodiments of the pulmonary nodule in CT image detecting method, and details are not described herein again.

The present disclosure further provides an equipment for detecting pulmonary nodule in CT image, the equipment includes the following parts. An obtaining module, being configured to obtain a CT image to be detected, performing a pixel segmentation processing on the CT image through a pre-stored three-dimensional convolutional neural pixel segmentation network, obtaining a probability graph corresponding to the CT image, and obtaining a candidate nodule region by marking a connected domain on the probability graph. And a model amalgamating module, being configured to predict the candidate nodule region by various pre-stored prediction models corresponding to different three-dimensional convolutional neural network classifiers, to obtain various probability prediction values of the candidate nodule region, and performing fusion processing on the various probability prediction values to obtain a classification result of the candidate nodule region.

The specific embodiment of the pulmonary nodule in CT image detecting equipment of this disclosure is basically the same as the above embodiments of the pulmonary nodule in CT image detecting method, and details are not described herein again.

The present disclosure provides a computer-readable storage medium that stores one or more programs, which can be executed by one or more processors to perform blocks in above embodiments of the pulmonary nodule in CT image detecting method.

The specific embodiment of the computer-readable storage medium of this disclosure is basically the same as the above embodiments of the pulmonary nodule in CT image detecting method, and details are not described herein again.

The foregoing description merely portrays some illustrative embodiments according to the disclosure and therefore is not intended to limit the patentable scope of the disclosure. Any equivalent structural or flow transformations that are made taking advantage of the specification and accompanying drawings of the disclosure and any direct or indirect applications thereof in other related technical fields shall all fall in the scope of protection of the disclosure.

What is claimed is:

1. A method for detecting pulmonary nodule in computed tomograph image, wherein the method comprises:
    obtaining a computed tomography image to be detected, performing a pixel segmentation processing on the computed tomography image through a pre-stored three-dimensional convolutional neural pixel segmentation network, to obtain a probability graph corresponding to the computed tomography image, and obtaining a candidate nodule region by marking a connected domain on the probability graph; and
    predicting the candidate nodule region by various pre-stored prediction models corresponding to different three-dimensional convolutional neural network classifiers, to obtain various probability prediction values of the candidate nodule region, and performing fusion processing on the various probability prediction values to obtain a classification result of the candidate nodule region;
    wherein the operation of performing a pixel segmentation processing on the computed tomography image through a pre-stored three-dimensional convolutional neural pixel segmentation network, to obtain a probability graph corresponding to the computed tomography image, and obtaining a candidate nodule region by marking a connected domain on the probability graph comprises:
    region dividing the computed tomography image in a preset size on to obtain sub-regions of the computed tomography image, respectively down-sampling the sub-regions for preset number of times by the pre-stored three-dimensional pixel segmentation network, and up-sampling the sub-regions for the same preset number of times after the sub-regions being down-sampled;
    performing feature-bridging and amalgamation processing on the sub-regions obtained respectively after the down-sampling process and the up-sampling process, forming sub probability-graphs that having the same size as the sub-regions;
    splicing each sub-probability graph for restoration to obtain the probability map corresponding to the computed tomography image; and
    marking a connected domain on the probability map corresponding to the computed tomography image, to obtain the candidate nodule region.

2. The method of claim 1, wherein down-sampling the sub-regions comprises convoluting, activating, batch standardizing, and pooling processing the sub-regions, and up-sampling the sub-regions comprises de-convoluting, activating, batch standardizing, and pooling processing the sub-regions after the sub-regions being down-sampled.

3. The method of claim 2, further comprising, prior to the operation of obtaining a computed tomography image to be detected, performing a pixel segmentation processing on the computed tomography image through a pre-stored three-dimensional convolutional neural pixel segmentation network:
    collecting computed tomography image sample data online through multiple processes, taking the collected computed tomography image sample data as a first sample data, and using the first sample data as input data to perform a training on the three-dimensional convolutional neural pixel segmentation network and the three-dimensional convolutional neural network classifier, to obtain hard negative sample data, wherein the hard negative sample data is the unsuccessfully predicted sample data in the first sample data;
    performing multiple translation and horizontal flip operations on the hard negative sample data to increase the proportion of the hard negative sample data in the first sample data, and taking the sample data that increase the proportion of the hard negative sample data as a second sample data;
    using the second sample data as input data to train the three-dimensional convolutional neural pixel segmentation network and the three-dimensional convolutional neural network classifier multiple times; and
    when the predicted accuracy of the trained three-dimensional convolutional neural pixel segmentation network and the trained three-dimensional convolutional neural network classifier reaches a first target accuracy rate and a second target accuracy rate respectively, executing the operation of obtaining the computed tomography image to be detected.

4. The method of claim 1, wherein the operation of performing fusion processing on the various probability prediction values to obtain a classification result of the candidate nodule region comprises:
    averaging the various probability prediction values and obtaining a target probability prediction value of the candidate nodule region; and
    comparing the target probability prediction value with a pre-stored threshold value, obtaining a comparison result, and obtaining the classification result of the candidate nodule region based on the comparison result, wherein the pre-stored threshold value is determined according to a receiver operating characteristic curve corresponding to the three-dimensional convolutional neural network.

5. The method of claim 4, further comprising, subsequent to obtaining a target probability prediction value of the candidate nodule region:
outputting the target probability prediction value and generating a target prompt message.

6. The method of claim 5, further comprising, prior to the operation of obtaining a computed tomography image to be detected, performing a pixel segmentation processing on the computed tomography image through a pre-stored three-dimensional convolutional neural pixel segmentation network:
collecting computed tomography image sample data online through multiple processes, taking the collected computed tomography image sample data as a first sample data, and using the first sample data as input data to perform a training on the three-dimensional convolutional neural pixel segmentation network and the three-dimensional convolutional neural network classifier, to obtain hard negative sample data, wherein the hard negative sample data is the unsuccessfully predicted sample data in the first sample data;
performing multiple translation and horizontal flip operations on the hard negative sample data to increase the proportion of the hard negative sample data in the first sample data, and taking the sample data that increase the proportion of the hard negative sample data as the second sample data;
using the second sample data as input data to training the three-dimensional convolutional neural pixel segmentation network and the three-dimensional convolutional neural network classifier multiple times; and
when the predicted accuracy of the trained three-dimensional convolutional neural pixel segmentation network and the three-dimensional convolutional neural network classifier after training reaches a first target accuracy rate and a second target accuracy rate respectively, executing the operation of obtaining the computed tomography image to be detected.

7. The method of claim 4, further comprising, prior to the operation of obtaining a computed tomography image to be detected, performing a pixel segmentation processing on the computed tomography image through a pre-stored three-dimensional convolutional neural pixel segmentation network:
collecting computed tomography image sample data online through multiple processes, taking the collected computed tomography image sample data as a first sample data, and using the first sample data as input data to perform a training on the three-dimensional convolutional neural pixel segmentation network and the three-dimensional convolutional neural network classifier, to obtain hard negative sample data, wherein the hard negative sample data is the unsuccessfully predicted sample data in the first sample data;
performing multiple translation and horizontal flip operations on the hard negative sample data to increase the proportion of the hard negative sample data in the first sample data, and taking the sample data that increase the proportion of the hard negative sample data as the second sample data;
using the second sample data as input data to train the three-dimensional convolutional neural pixel segmentation network and the three-dimensional convolutional neural network classifier multiple times; and
when the predicted accuracy of the three-dimensional convolutional neural pixel segmentation network and the trained three-dimensional convolutional neural network classifier reaches the first target accuracy rate and a second target accuracy rate respectively, executing the operation of obtaining the computed tomography image to be detected.

8. The method of claim 1, wherein the operation of predicting the candidate nodule region by various pre-stored prediction models corresponding to different three-dimensional convolutional neural network classifiers, to obtain various probability prediction values of the candidate nodule region, comprises:
down-sampling and full-connecting the candidate nodule region by various pre-stored prediction models corresponding to the different three-dimensional convolutional neural network classifiers, to obtain various probability prediction values of the candidate nodule region;
wherein down-sampling the candidate nodule region comprises convoluting, activating, batch standardizing, and pooling processing the candidate nodule region.

9. The method of claim 8, further comprising, prior to the operation of obtaining a computed tomography image to be detected, performing a pixel segmentation processing on the computed tomography image through a pre-stored three-dimensional convolutional neural pixel segmentation network:
collecting computed tomography image sample data online through multiple processes, taking the collected computed tomography image sample data as a first sample data, and using the first sample data as input data to perform a training on the three-dimensional convolutional neural pixel segmentation network and the three-dimensional convolutional neural network classifier, to obtain hard negative sample data, wherein the hard negative sample data is the unsuccessfully predicted sample data in the first sample data;
performing multiple translation and horizontal flip operations on the hard negative sample data to increase the proportion of the hard negative sample data in the first sample data, and taking the sample data that increase the proportion of the hard negative sample data as the second sample data;
using the second sample data as input data to training the three-dimensional convolutional neural pixel segmentation network and the three-dimensional convolutional neural network classifier multiple times; and
when the predicted accuracy of the trained three-dimensional convolutional neural pixel segmentation network and the trained three-dimensional convolutional neural network classifier after training reaches a first target accuracy rate and a second target accuracy rate respectively, executing the operation of obtaining the computed tomography image to be detected.

10. The method of claim 1, further comprising, prior to the operation of obtaining a computed tomography image to be detected, performing a pixel segmentation processing on the computed tomography image through a pre-stored three-dimensional convolutional neural pixel segmentation network:
collecting computed tomography image sample data online through multiple processes, taking the collected computed tomography image sample data as a first sample data, and using the first sample data as input data to perform a training on the three-dimensional convolutional neural pixel segmentation network and the three-dimensional convolutional neural network classifier, to obtain hard negative sample data, wherein the hard negative sample data is the unsuccessfully predicted sample data in the first sample data;

performing multiple translation and horizontal flip operations on the hard negative sample data to increase the proportion of the hard negative sample data in the first sample data, and taking the sample data that increase the proportion of the hard negative sample data as a second sample data;

using the second sample data as input data to train the three-dimensional convolutional neural pixel segmentation network and the three-dimensional convolutional neural network classifier multiple times; and when the predicted accuracy of the trained three-dimensional convolutional neural pixel segmentation network and the trained three-dimensional convolutional neural network classifier reaches a first target accuracy rate and a second target accuracy rate respectively, executing the operation of obtaining the computed tomography image to be detected.

11. The method of claim 1, further comprising, prior to the operation of obtaining a computed tomography image to be detected, performing a pixel segmentation processing on the computed tomography image through a pre-stored three-dimensional convolutional neural pixel segmentation network:

collecting computed tomography image sample data online through multiple processes, taking the collected computed tomography image sample data as a first sample data, and using the first sample data as input data to perform a training on the three-dimensional convolutional neural pixel segmentation network and the three-dimensional convolutional neural network classifier, to obtain hard negative sample data, wherein the hard negative sample data is the unsuccessfully predicted sample data in the first sample data;

performing multiple translation and horizontal flip operations on the hard negative sample data to increase the proportion of the hard negative sample data in the first sample data, and taking the sample data that increase the proportion of the hard negative sample data as the second sample data;

using the second sample data as input data to training the three-dimensional convolutional neural pixel segmentation network and the three-dimensional convolutional neural network classifier multiple times; and when the predicted accuracy of the trained three-dimensional convolutional neural pixel segmentation network and the trained three-dimensional convolutional neural network classifier after training reaches a first target accuracy rate and a second target accuracy rate respectively, executing the operation of obtaining the computed tomography image to be detected.

12. A device for detecting pulmonary nodule in computed tomography image, wherein the device comprises a memory, a processor, a communication bus, and a detecting program for detecting pulmonary nodule in computed tomography image stored in the memory;

the communication bus being configured to facilitate a communication connection between the processor and the memory;

the processor being configured to execute the detecting program for detecting pulmonary nodule in computed tomography image to perform the following operations:

obtaining a computed tomography image to be detected, performing a pixel segmentation processing on the computed tomography image through a pre-stored three-dimensional convolutional neural pixel segmentation network, to obtain a probability graph corresponding to the computed tomography image, and obtaining a candidate nodule region by marking a connected domain on the probability graph; and predicting the candidate nodule region by various pre-stored prediction models corresponding to different three-dimensional convolutional neural network classifiers, to obtain various probability prediction values of the candidate nodule region, and performing fusion processing on the various probability prediction values to obtain a classification result of the candidate nodule region;

wherein the operation of performing a pixel segmentation processing on the computed tomography image through a pre-stored three-dimensional convolutional neural pixel segmentation network, to obtain a probability graph corresponding to the computed tomography image, obtaining a candidate nodule region by marking a connected domain on the probability graph comprises:

region dividing the computed tomography image in a preset size on to obtain sub-regions of the computed tomography image, respectively down-sampling the sub-regions for preset number of times by the pre-stored three-dimensional pixel segmentation network, and up-sampling the sub-regions for the same preset number of times after the sub-regions being down-sampled;

performing feature-bridging and amalgamation processing on the sub-regions obtained respectively after the down-sampling process and the up-sampling process, forming sub probability-graphs that having the same size as the sub-regions; and splicing each sub-probability graph for restoration to obtain the probability map corresponding to the computed tomography image; and marking a connected domain on the probability map corresponding to the computed tomography image, to obtain the candidate nodule region.

13. The device of claim 12, wherein down-sampling the sub-regions comprises convoluting, activating, batch standardizing, and pooling processing the sub-regions, and up-sampling the sub-regions comprises de-convoluting, activating, batch standardizing, and pooling processing the sub-regions after the sub-regions being down-sampled.

14. The device of claim 12, wherein the operation of performing fusion processing on the various probability prediction values to obtain a classification result of the candidate nodule region comprises:

averaging the various probability prediction values and obtaining a target probability prediction value of the candidate nodule region; and comparing the target probability prediction value with a pre-stored threshold value, obtaining a comparison result, and obtaining the classification result of the candidate nodule region based on the comparison result, wherein the pre-stored threshold value is determined according to a receiver operating characteristic curve corresponding to the three-dimensional convolutional neural network.

15. The device of claim 14, further comprising, subsequent to the block of obtaining a target probability prediction value of the candidate nodule region:

outputting the target probability prediction value and generating a target prompt message.

16. The device of claim 12, wherein the operation of predicting the candidate nodule region by various pre-stored prediction models corresponding to different three-dimensional convolutional neural network classifiers, to obtain various probability prediction values of the candidate nodule region comprises:
   down-sampling and full-connecting the candidate nodule region by various pre-stored prediction models corresponding to the different three-dimensional convolutional neural network classifiers, to obtain various probability prediction values of the candidate nodule region; and
   wherein down-sampling the candidate nodule region comprises convoluting, activating, batch standardizing, and pooling processing the candidate nodule region.

17. The device of claim 12, further comprising, prior to the operation of obtaining a computed tomography image to be detected, performing a pixel segmentation processing on the computed tomography image through a pre-stored three-dimensional convolutional neural pixel segmentation network:
   collecting computed tomography image sample data online through multiple processes, taking the collected computed tomography image sample data as a first sample data, and using the first sample data as input data to perform a training on the three-dimensional convolutional neural pixel segmentation network and the three-dimensional convolutional neural network classifier, to obtain hard negative samples, wherein the hard negative sample is the unsuccessfully predicted sample in the first sample data;
   performing multiple translation and horizontal flip operations on the hard negative sample data to increase the proportion of the hard negative sample data in the first sample data, and taking the sample data that increase the proportion of the hard negative sample data as a second sample data;
   using the second sample data as input data to train the three-dimensional convolutional neural pixel segmentation network and the three-dimensional convolutional neural network classifier multiple times; and
   when the predicted accuracy of the trained three-dimensional convolutional neural pixel segmentation network and the trained three-dimensional convolutional neural network classifier reaches a first target accuracy rate and a second target accuracy rate respectively, executing the operation of obtaining the computed tomography image to be detected.

18. A non-transitory readable storage medium, storing a detecting program for detecting pulmonary nodule in computed tomography image, which when executed by a processor performing the following operations:
   obtaining a computed tomography image to be detected, performing a pixel segmentation processing on the computed tomography image through a pre-stored three-dimensional convolutional neural pixel segmentation network, to obtain a probability graph corresponding to the computed tomography image, and obtaining a candidate nodule region by marking a connected domain on the probability graph; and
   predicting the candidate nodule region by various pre-stored prediction models corresponding to different three-dimensional convolutional neural network classifiers, to obtain various probability prediction values of the candidate nodule region, and performing fusion processing on the various probability prediction values to obtain a classification result of the candidate nodule region;
   wherein the operation of performing a pixel segmentation processing on the computed tomography image through a pre-stored three-dimensional convolutional neural pixel segmentation network, to obtain a probability graph corresponding to the computed tomography image, obtaining a candidate nodule region by marking a connected domain on the probability graph comprises:
   region dividing the computed tomography image in a preset size to obtain sub-regions of the computed tomography image, respectively down-sampling the sub-regions for preset number of times by the pre-stored three-dimensional pixel segmentation network, and up-sampling the sub-regions for the same preset number of times after the the sub-regions being down-sampled;
   performing feature-bridging and amalgamation processing on the sub-regions obtained respectively after the down-sampling process and the up-sampling process, forming sub probability-graphs that having the same size as the sub-regions;
   splicing each sub-probability graph for restoration to obtain the probability map corresponding to the computed tomography image; and
   marking a connected domain on the probability map corresponding to the computed tomography image, to obtain a candidate nodule region.

* * * * *